(12) United States Patent
Sarver

(10) Patent No.: US 7,938,537 B2
(45) Date of Patent: May 10, 2011

(54) CONTINUOUS TWO-DIMENSIONAL CORNEAL TOPOGRAPHY TARGET

(75) Inventor: Edwin J. Sarver, Carbondale, IL (US)

(73) Assignee: Sarver & Associates, Inc., Carbondale, IL (US)

( * ) Notice: Subject to any disclaimer, the term of this patent is extended or adjusted under 35 U.S.C. 154(b) by 0 days.

(21) Appl. No.: 12/723,198

(22) Filed: Mar. 12, 2010

(65) Prior Publication Data

US 2010/0182568 A1    Jul. 22, 2010

Related U.S. Application Data

(63) Continuation-in-part of application No. 12/357,002, filed on Jan. 21, 2009, now Pat. No. 7,740,356.

(51) Int. Cl.
*A61B 3/10* (2006.01)
(52) U.S. Cl. ....................................................... 351/212
(58) Field of Classification Search .................. 351/205, 351/212, 247
See application file for complete search history.

(56) References Cited

U.S. PATENT DOCUMENTS

| 4,493,539 | A | 1/1985 | Cannon, Jr. |
| 4,863,260 | A | 9/1989 | Gersten |
| 4,995,716 | A | 2/1991 | Warnicki |
| 5,668,623 | A | 9/1997 | Sakurai et al. |
| 5,841,511 | A | 11/1998 | D'Souza |
| 5,912,723 | A | 6/1999 | Maddess |
| 6,116,738 | A | 9/2000 | Rorabaugh |
| 6,926,408 | B2 | 8/2005 | Sarver |
| 7,219,998 | B2 * | 5/2007 | Grove et al. .................. 351/212 |
| 7,611,245 | B2 * | 11/2009 | Carbonari ..................... 351/212 |
| 7,740,356 | B2 | 6/2010 | Sarver |

* cited by examiner

*Primary Examiner* — Huy K Mai
(74) *Attorney, Agent, or Firm* — McHale & Slavin, P.A.

(57) ABSTRACT

A two-dimensional reflection pattern suitable for corneal topography that uses sinusoidal profiles of both intensity and color values. The technique provides a more robust image processing due to the ability to apply digital band pass filters, continuous data for improved surface reconstruction, and the ability to directly measure the meridian of the reflection pattern source point when the corneal surface normal does not lie in the meridian of the measurement instrument.

12 Claims, 4 Drawing Sheets

CONTINUOUS TWO-DIMENSIONAL CORNEAL TOPOGRAPHY TARGET

PRIORITY CLAIM AND RELATED PRIOR ART

This application is a CIP of patent application Ser. No. 12/357,002 entitled Monochromatic multi-resolution corneal topography target filed Jan. 21, 2009, now U.S. Pat. No. 7,740,356 the contents of which are incorporated herein by reference. This application is also related to U.S. Pat. No. 6,926,408 the contents of which are incorporated herein by reference.

FIELD OF THE INVENTION

This invention is directed to the field of eye examination.

BACKGROUND OF THE INVENTION

The human cornea provides about two-thirds of the refraction of the eye. Thus, its shape is of great interest to optometrists and ophthalmologists who must provide a patient with sharp vision. A device that measures the shape of the cornea is referred to as a corneal topographer. Although there are various methods to measure the cornea, the most popular commercial systems are based on the principle of measuring a pattern reflected off the cornea. The pattern most often used for this purpose is a set of concentric rings. One problem with concentric ring patterns is that it is difficult to know the exact point correspondence between a point on the reflected pattern source and its image reflected off the cornea. If the cornea is not axially symmetric, the surface normal of a point on the cornea will not lie in the meridional plane of the measurement system and thus, the point of light originating on the reflected pattern source will not lie in the same meridional plane. To directly measure the point correspondence, polar and rectangular checkerboard patterns have also been proposed, but have not become popular in commercial systems.

Usually these various reflection patterns are monochrome (black and white), but color has been included in some cases. In one commercial system concentric rings are of alternating colors of red, green, and blue. In a research system, a random color grid was employed. In cases where color is used, the motivation is to provide a more robust method of correctly identifying the correspondence between a point on the reflection pattern source and the image reflected off the cornea and digitized for computer processing.

The reflection patterns to date have been discrete in some way and the computer image processing task is to find edges or peaks in the image which correspond to points in the source. The results of the computer image processing can yield a set of point correspondences that is not always correct. Such image processing errors would lead to large measurement errors in subsequent reconstruction processing. Even if the point correspondence is correct, the accuracy of reconstruction algorithms is related to the spacing of the data. Generally, if the discrete points are far apart the reconstruction error will be larger than would be obtained if the points were close together. Because of this general observation, continuous data would provide the most accurate surface reconstruction measurements.

SUMMARY OF THE INVENTION

The aim of this invention is to provide an improved means to generate a continuous two-dimensional reflection pattern suitable for corneal topography that uses sinusoidal profiles of both intensity and color values. The benefits of this technique are more robust image processing due to the ability to apply digital band pass filters, continuous data for improved surface reconstruction, and the ability to directly measure the meridian of the reflection pattern source point when the corneal surface normal does not lie in the meridian of the measurement instrument.

An objective of this invention is to disclose the use of a corneal topography reflective target that employs contrasting circles to better support the direct measurement of skew rays.

Another objective of this invention is to provide a technique for more robust image processing by applying digital band pass filters.

Still another objective of this invention is to provide a technique for more robust image processing by allowing continuous data for improved surface reconstruction.

Yet still another objective of this invention is to provide a technique for more robust image processing by directly measuring the meridian of the reflection pattern source point when the corneal surface normal does not lie in the meridian of the measurement instrument.

Other objectives and advantages of this invention will become apparent from the following description taken in conjunction with the accompanying drawings wherein are set forth, by way of illustration and example, certain embodiments of this invention.

DETAILED DESCRIPTION OF THE INVENTION

This application discloses a two-dimensional reflection pattern suitable for corneal topography wherein the reflection pattern has contrasting circles to better support the direct measurement of skew rays. Co-pending application Ser. No. 12/357,002, contents of which are incorporated herein by reference, discloses the use of two-dimensional reflection patterns.

Figure 1:
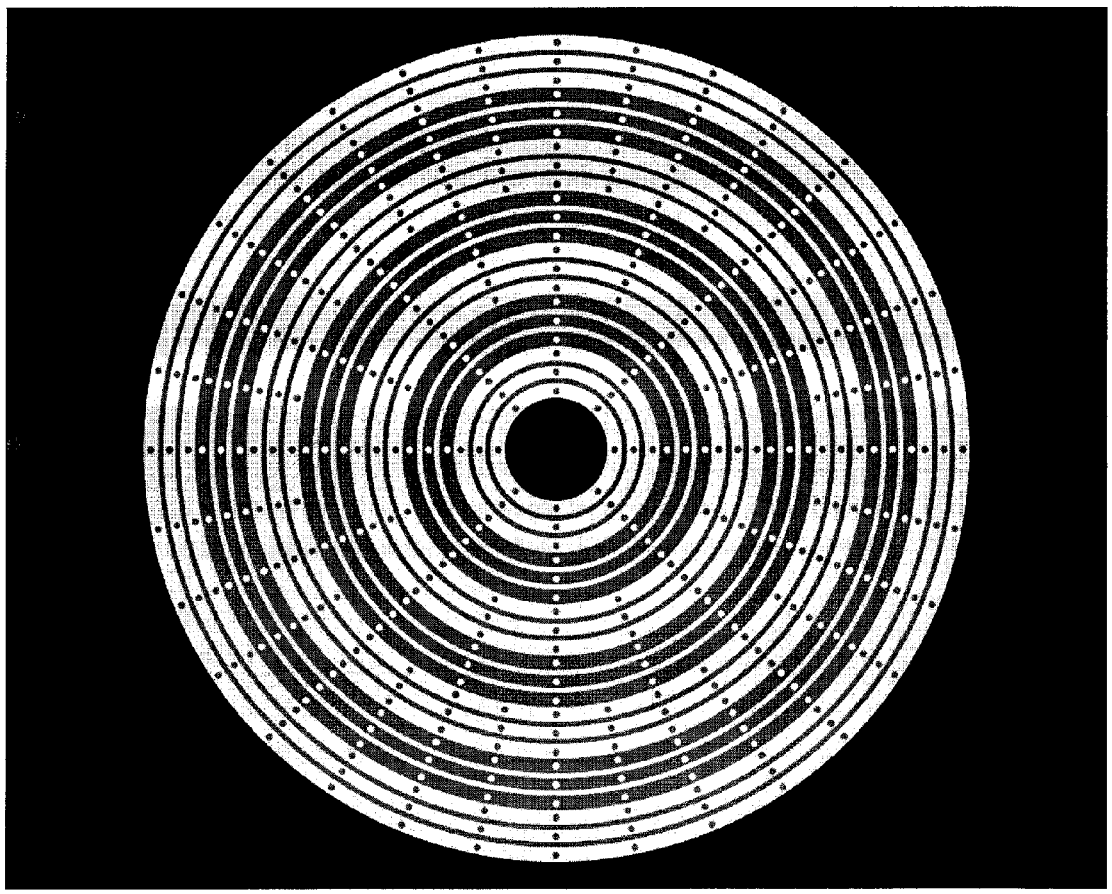
FIG. 1 illustrates a multi-resolution corneal topography pattern with contrasting circles placed at various meridians and starting at various radial distances.

Skew rays occur when a portion of a target reflects of a portion of a cornea such that the surface normal at the cornea is not contained in the meridional plane of the corneal point. This can happen, for example, on the side of a corneal bump such as that caused by keratoconus. To directly measure the skew ray angle, we add contrasting circles along certain meridians of the multi-resolution target. This is illustrated in FIG. 1 depicting multi-resolution corneal topography pattern with contrasting circles placed at various meridians and starting at various radial distances.

Figure 2:
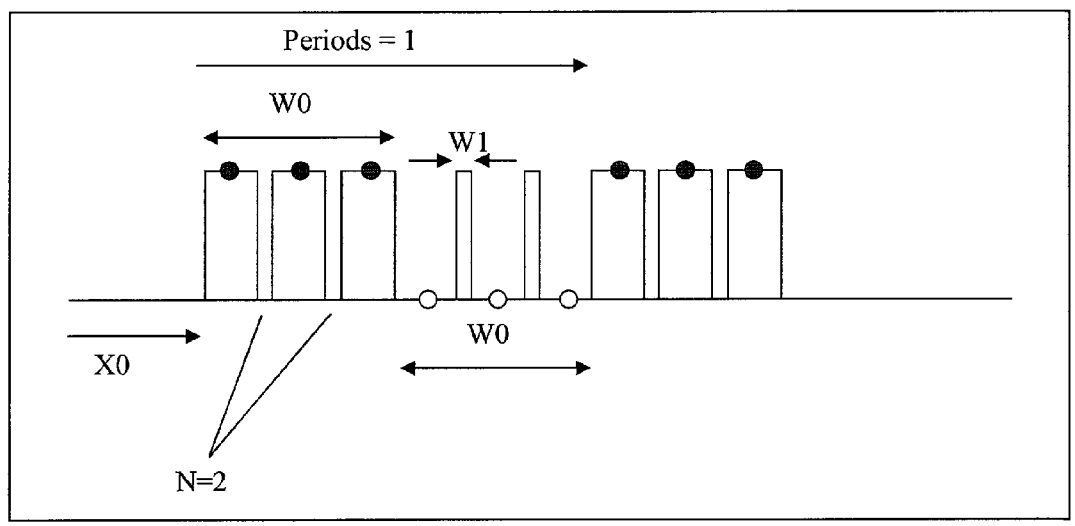
FIG. 2 is a graphical illustration of the parameters for preferred embodiment target.

The contrasting circles are located between the high-resolution square pulses within a low-resolution square pulse. FIG. 2 illustrates the parameters for preferred embodiment target. These parameters are with respect to the captured image reflected off the cornea. The target edges are then calculated by ray tracing or other means, back to the hardware surface. The location of the locally contrasting circles are indicated by the filled circles.

Figure 3:
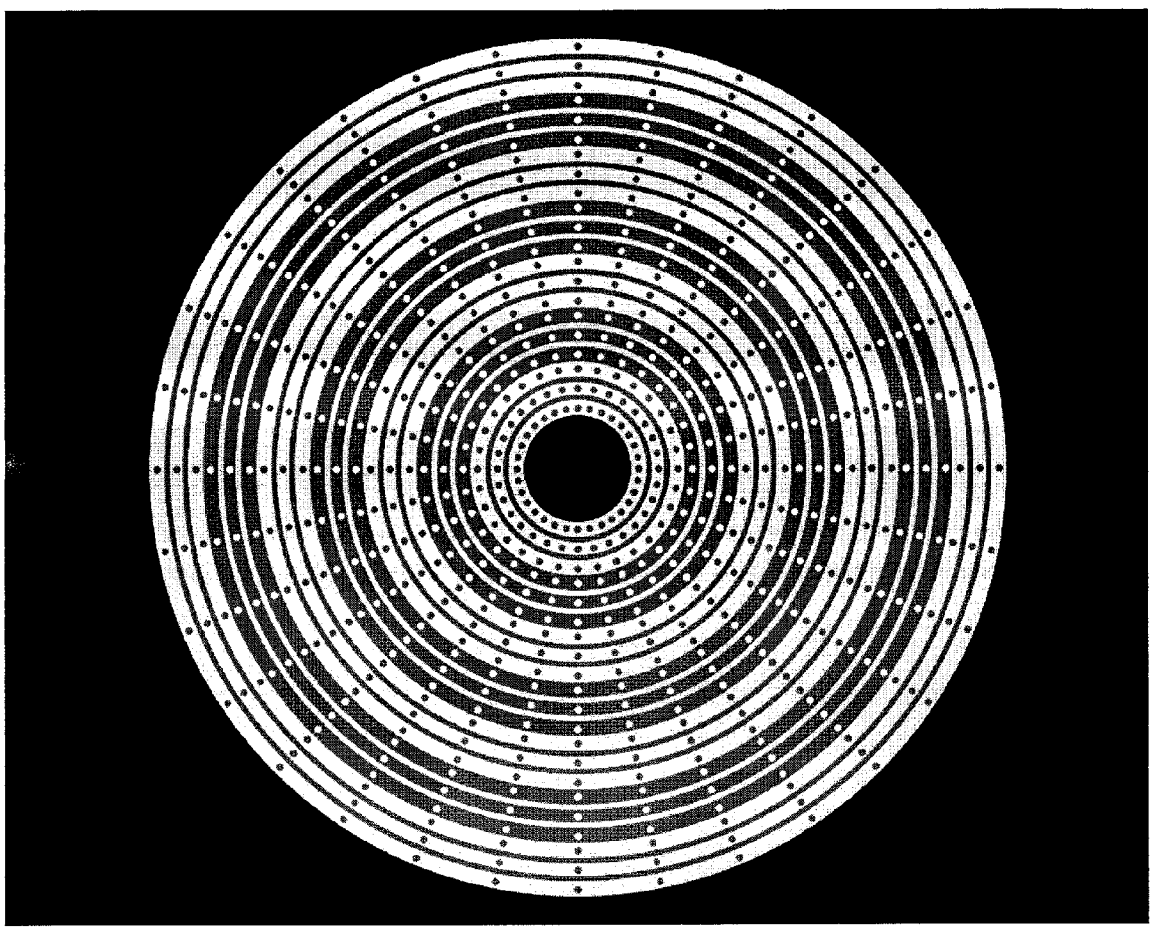
FIG. 3 illustrates a skew ray target wherein all dot meridians are allowed to start in the center ring.

The dot diameter is equal to half the width of the region between the high-resolution square pulses and they are centered midway between the high-resolution square pulses. As illustrated in FIG. 1, we do not allow all dot meridians to start in the center as that would cause difficulty in finding the image features since they would be too close together. An example of a "bad" skew ray target is illustrated in FIG. 3 where all dot meridians are allowed to start in the center ring.

The number of contrasting dot meridians and the radial starting point of the meridians can be varied according to aesthetic appeal of the target as well as anticipated magnitude and location of skew rays to be measured. For example, for surfaces with slight skew ray angles, the meridians can be placed close together (but far enough apart to be detected with image processing) while for surfaces with larger skew ray angles the meridians should be placed further apart.

Figure 4:
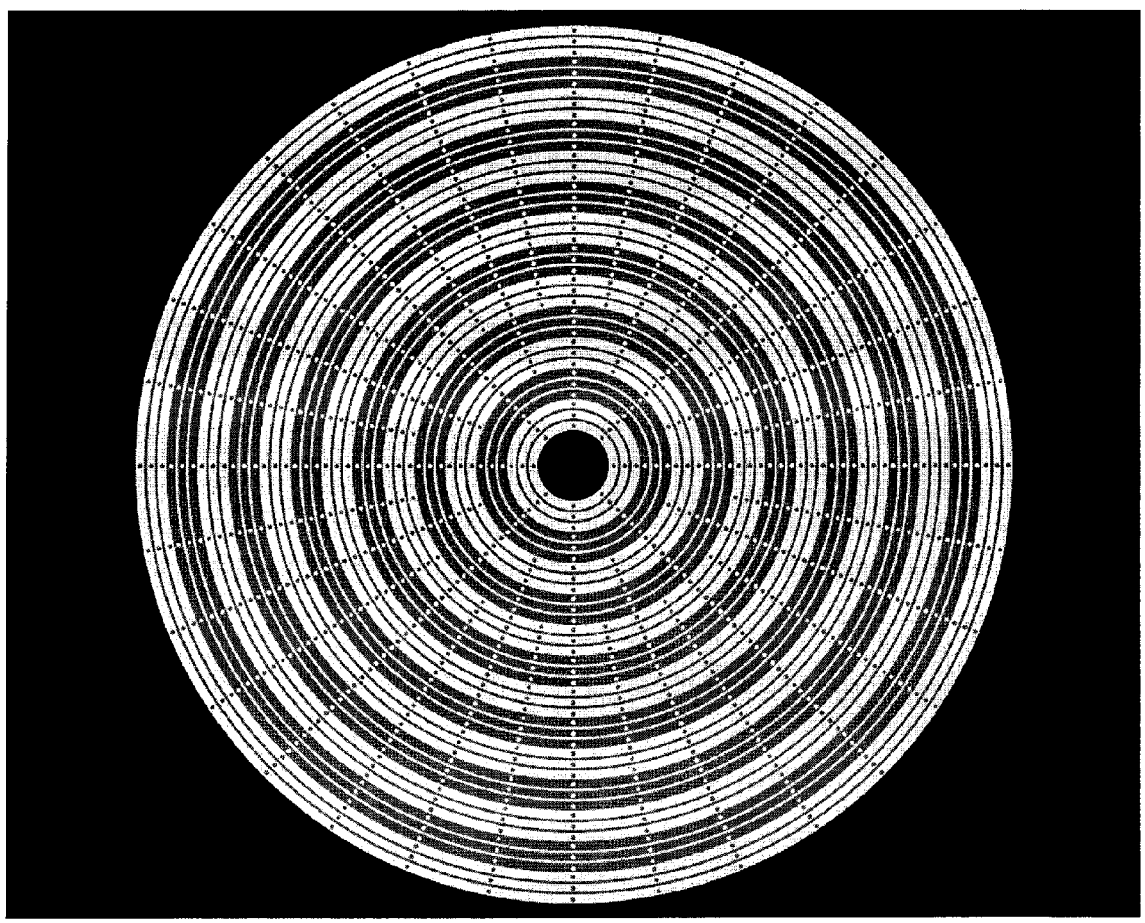
FIG. 4 illustrates the skew ray multi-resolution target of the preferred embodiment.

For the wide range of corneas likely to be measured in a clinical setting, the pattern illustrated in FIG. 4 is the multi-resolution target with skew ray dot meridians of the preferred embodiment. Note that these patterns illustrate the reflected pattern off the surface (such as a human eye) being measured. The use of ray tracing analysis known to those skilled in the art is employed to determine the actual size and location of these features on the target.

The multi resolution rings can be illuminated and turned off as a group or illuminated and turned off individually. The contrasting skew ray dot patterns can also be illuminated and turned off as a group or illuminated and turned off individually.

The target can be manufactured using the techniques described in the previous multi-resolution corneal topography target patent disclosure. The software process is also a simple extension of the methods described in the previous disclosure.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

I claim:

1. A reflective pattern source for use with a corneal topography system for measuring the shape of the cornea of the eye comprising: a two dimensional surface having a circular reflective pattern of multi-resolution rings thereon for measuring reflected light from a cornea, said circular reflective pattern having sinusoidal profiles of both intensity and color values.

2. The corneal topography reflective target according to claim 1 wherein said reflective pattern is a function of multiple resolutions of measurements representing at least both the short radius of curvature and long radius of curvature of the cornea.

3. The corneal topography reflective target according to claim 1 wherein said circular reflective pattern provides for the direct measurement of skew rays.

4. The corneal topography reflective target according to claim 1 wherein said multi-resolution rings includes a series of contrasting skew ray dot patterns.

5. The corneal topography reflective target according to claim 4 wherein said contrasting skew ray dot patterns are positioned by placement along a predetermined radial position and a predetermined meridional location.

6. The corneal topography system of claim 4 wherein said contrasting skew ray dot patterns are illuminated and turned off as a group.

7. The corneal topography system of claim 4 wherein said contrasting skew ray dot patterns are illuminated and turned off individually.

8. The corneal topography system of claim 1 wherein said multi resolution rings are illuminated and turned off as a group.

9. The corneal topography system of claim 1 wherein said multi-resolution rings are illuminated and turned off individually.

10. The corneal topography system of claim 1 wherein said circular reflective pattern allows for improved image processing by applying digital band pass filters.

11. The corneal topography system of claim 1 wherein said circular reflective pattern allows for improved image processing by allowing continuous data for improved surface reconstruction.

12. The corneal topography system of claim 1 wherein said circular reflective pattern allows for improved image processing by directly measuring the meridian of the reflection pattern source point when the corneal surface normal does not lie in the meridian of the measurement instrument.

* * * * *